United States Patent [19]

Monfort et al.

[11] Patent Number: 4,890,611
[45] Date of Patent: Jan. 2, 1990

[54] ENDARTERECTOMY APPARATUS AND METHOD

[75] Inventors: Michelle Y. Monfort, Los Altos; Albert K. Chin, Palo Alto; Kenneth H. Mollenauer, Santa Clara, all of Calif.

[73] Assignee: Thomas J. Fogarty, Portola Valley, Calif.

[21] Appl. No.: 178,029

[22] Filed: Apr. 5, 1988

[51] Int. Cl.⁴ ............................................. A61B 17/22
[52] U.S. Cl. .................................... 606/159; 124/774; 606/160
[58] Field of Search ............... 128/304, 305, 341, 344, 128/348.1, 303 R, 774; 604/53, 101, 104, 264, 266, 267; 73/862.53, 862.39, 862.62

[56] References Cited

U.S. PATENT DOCUMENTS

| 42,801 | 5/1864 | Sleppy | 73/862.62 |
| 2,701,559 | 2/1955 | Cooper . | |
| 2,943,626 | 7/1960 | Dormia . | |
| 3,108,593 | 10/1963 | Glassman . | |
| 3,108,594 | 10/1963 | Glassman . | |
| 3,811,446 | 5/1974 | Lerwick et al. . | |
| 3,996,938 | 12/1976 | Clark, III | 128/348 |
| 4,030,503 | 6/1977 | Clark, III | 128/304 |
| 4,046,150 | 9/1977 | Schwarts et al. . | |
| 4,287,890 | 9/1981 | Fogarty . | |
| 4,290,427 | 9/1981 | Chin . | |
| 4,315,511 | 2/1982 | Chin . | |
| 4,452,244 | 6/1984 | Chin . | |
| 4,559,927 | 12/1985 | Chin . | |
| 4,574,781 | 3/1986 | Chin | 128/304 |
| 4,621,636 | 11/1986 | Fogarty . | |
| 4,630,609 | 12/1986 | Chin . | |
| 4,706,671 | 11/1987 | Weinrib | 128/341 |
| 4,721,507 | 1/1988 | Chin | 604/100 |
| 4,762,130 | 8/1988 | Fogarty | 128/348 |
| 4,820,283 | 4/1989 | Schickling et al. | 604/280 |

FOREIGN PATENT DOCUMENTS 3532653 4/1987 Fed. Rep. of Germany ...... 128/344
584856 12/1977 U.S.S.R. .

OTHER PUBLICATIONS

"Technical Features in Fundarterectom"; Leven, Harold Surgery, vol. 57, No. 1 (1/1965), pp. 22-27.
PCT Application WO 83/00997, International Publication Date: 3/31/83.

Primary Examiner—Michael H. Thaler
Assistant Examiner—William Lewis
Attorney, Agent, or Firm—Limbach, Limbach & Sutton

[57] ABSTRACT

Radially expansible, helically configured wire loops are employed to grip and shear arteriosclerotic deposits from the lumen of an artery wall. Shearing action is achieved by pulling the loops through the artery by means of a handle which is freely rotatable to avoid the application of torsional forces to the loops. A shear force gauge may be provided to measure and limit the pulling force applied to the loops.

3 Claims, 2 Drawing Sheets

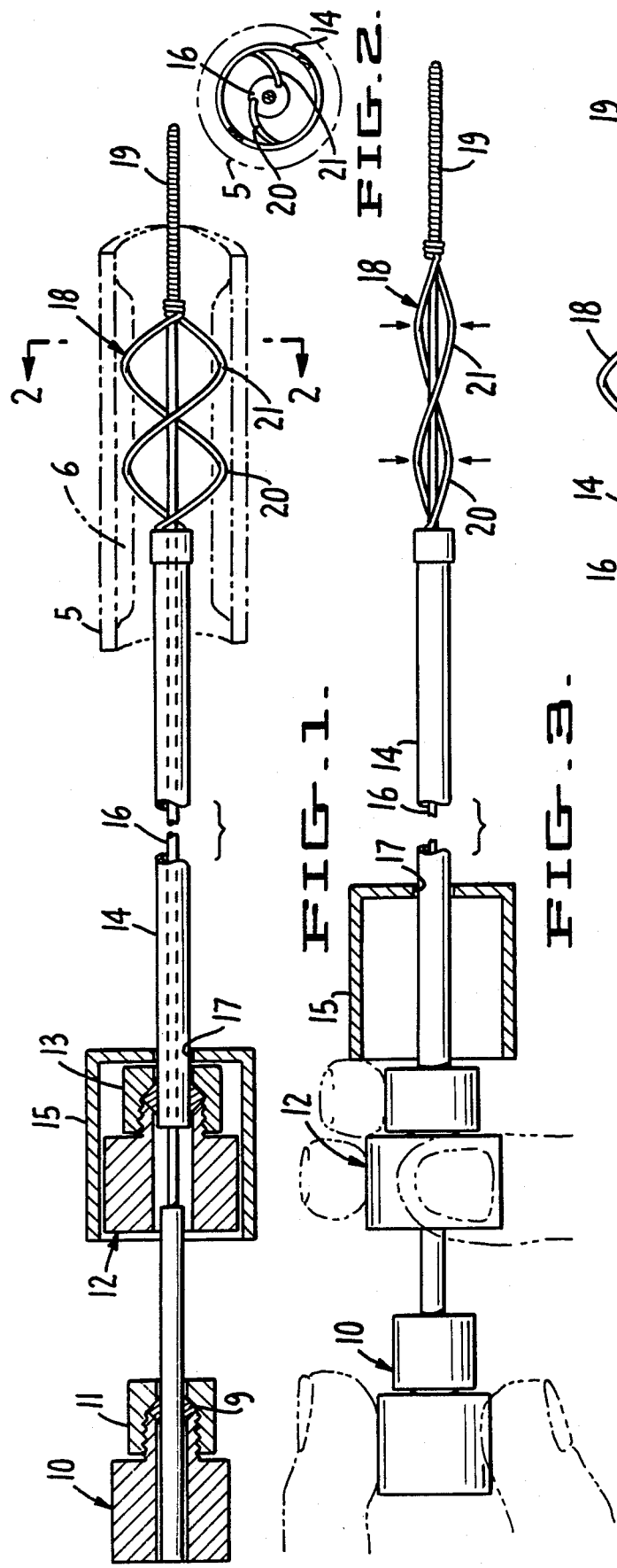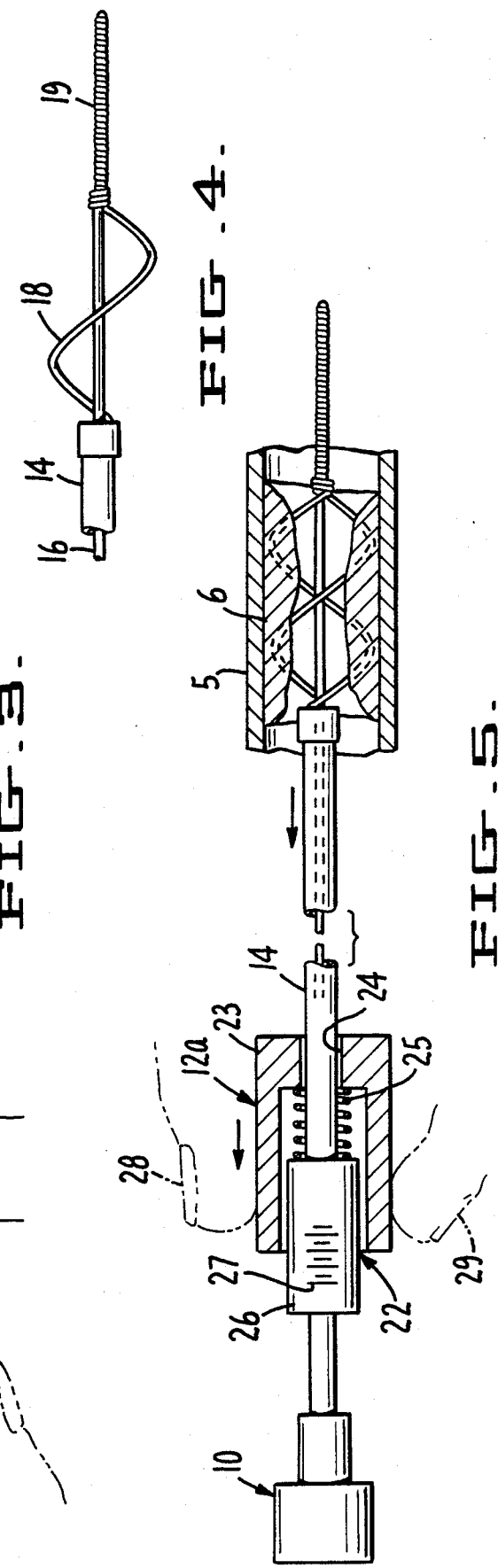

ENDARTERECTOMY APPARATUS AND METHOD

BACKGROUND OF THE INVENTION

This invention relates to an apparatus and method for shearing arteriosclerotic deposits from the lumen of an occluded artery.

The correction of arteriosclerotic deposits and occlusions has been an object of much medical research. Heretofore, correction has been achieved by cutting, stripping or compacting the deposit. See U.S. Pat. Nos. 4,452,244; 4,574,781; and 4,630,609. The present invention differs markedly from the prior art in that it shears the deposit from the diseased vessel. Prior art which is material to this invention consists of U.S. Pat. Nos. 2,943,626; 3,108,593; 3,108,594; 3,811,446; and 4,046,150. All relate to entrapment devices which employ wire cages for removing objects from body passages. U.S. pat. No. 3,811,446 in particular discloses use of a single inexpansible wire loop for endarterectomy and a wire basket for debriding an artery. U.S. Pat. No. 2,943,626 discloses a wire basket for the extraction of foreign bodies, but makes no suggestion of endarterectomy.

SUMMARY OF THE INVENTION

In its broadest aspects, the apparatus comprises a selectively expansible gripper which may be inserted into an artery in a contracted condition and, once within the artery, radially expanded to grip an arteriosclerotic deposit to be removed. The method provided by the apparatus enables the deposit to be sheared away from the vessel wall, without abrading the wall or damaging the artery or surrounding tissue.

One object of this invention is a decrease in complexity and duration of surgical procedures necessary to remove arteriosclerotic deposits from or bypass entirely heavily diseased arteries.

Another object of this invention is to provide an apparatus capable of shearing arteriosclerotic deposits from diseased arteries so as to leave a smoother, cleaner artery wall.

A further object of this invention is to provide a method for employing a shearing apparatus in the removal of arteriosclerotic deposits.

Other objects and aims of the invention will become clear upon further reading of the disclosure and claims.

DESCRIPTION OF THE DRAWINGS

FIG. 1 is a lateral view of one embodiment of the apparatus of the invention with parts shown in section, the shearing member expanded, and an artery being treated shown in phantom.

FIG. 2 is a cross-sectional view taken on the plane designated by line 2—2 of FIG. 1, showing the helical configuration of the expanded shearing member in an artery.

FIG. 3 is a lateral view of the apparatus in FIG. 1 showing the shearing member collapsed.

FIG. 4 is a lateral view of another embodiment of the shearing member of the invention.

FIG. 5 is a partial cutaway in lateral view of an embodiment of the apparatus similar to that of FIG. 1, which additionally incorporates a shear force gauge.

DESCRIPTION OF THE PREFERRED EMBODIMENT

Figure 6:
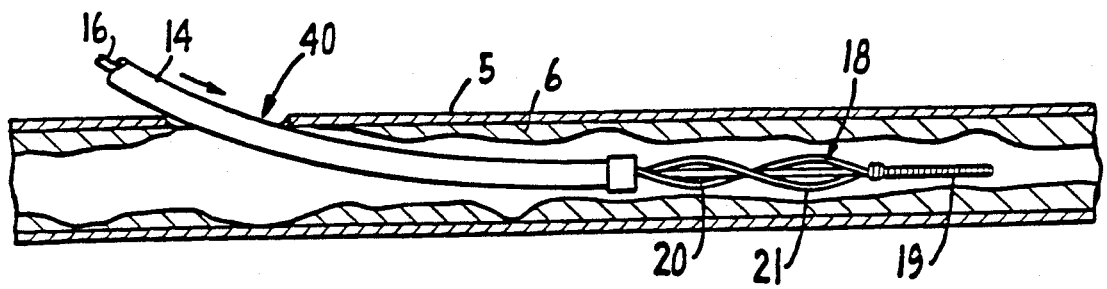
FIG. 6 is a view in diametral section through an occluded artery illustrating one method of preliminary emplacement of the apparatus with respect to the artery.

Turning to the drawings, the preferred embodiment of the shearing apparatus is illustrated in FIG. 1. As there shown, the apparatus is disposed within a diseased artery 5 having an arteriosclerotic deposit 6 therein. The apparatus comprises a handle 10, a grip 12, a flexible catheter 14, a pull cup 15, a flexible wire 16, and a shearing member 18. The shearing member 18 of the preferred embodiment comprises two helically configured loops 20 and 21, as shown in FIG. 2, although a single loop, as shown in FIG. 4, may suffice. The handle 10 is affixed to the proximal end of the wire 16 by means of a collet 11. The collet 11 is threadably received on the handle 10 and includes a compressible annular element 9 captured in compression imparting relationship to the wire 16. The grip 12 is affixed similarly to the proximal end of the catheter 14 by means of a collet 13 which captures an annular element 9 in compression imparting relationship to the catheter 14. Pull cup 15 is slidably and rotatably received on the catheter 14 through means of a passage 17 extending through the cup. The loops 20 and 21 are soldered or otherwise affixed to the distal portion of wire 16 so as to leave the apical portion of the wire 16 free from and distally external to the shearing member 18. A flexible tip 19 extends from the distal end of the wire 16 to facilitate guidance of the apparatus through narrow tortuous vessels. The loops 20 and 21 are suitably affixed at their remaining ends to the distal tip of the catheter 14 in such a position as to comport a helical configuration. The wire 16 passes freely through the length of the catheter 14 and is preferably made from spring stainless steel. The catheter may be made of any suitable flexible polymer material. Dacron is a preferred material and polyvinyl chloride is another. A typical O.D. for the catheter is 0.050 inches; a typical I.D. is 0.025 inches. The shearing member may be made of 0.018 inch diameter stainless steel spring wire and, in a typical embodiment, be moveable from a contracted condition having an O.D. of 0.083 inches to an expanded condition having an O.D. of 0.250 inches. With the latter dimensions typical dimensions for the length of the shearing member would be 0.70 inches in the condition when the member is contracted radially and 0.30 inches when the member is expanded radially. The expanded and contracted dimensions of the shearing member will be chosen to accommodate the diameter of the artery being treated.

The spring wire of which the shearing member 18 is fabricated is preformed into an expanded helical configuration, as depicted in FIGS. 1 and 4. It is radially contracted by pushing on the handle 10 relative to the grip 12, thereby forcing the wire 16 through the catheter 14 and extending length of the shearing member relative to the catheter's distal end, as shown in FIG. 3. Alternatively, the shearing member 18 may be radially expanded by pulling the handle 10 relative to the grip 12, thereby diminishing the wire's length relative to the distal end of the catheter.

In the embodiment shown in FIG. 5, a grip 12a embodying a shear force gauge 22 is substituted for the grip 12. The shear force gauge 22 permits the monitoring of tension applied to the catheter 14 and the delivery of a preset amount of shearing force to the vessel in order to reduce potential trauma and ensure that a sufficient vessel thickness remains after removal of the deposit. The gauge 22 comprises a cup element 23 having a passage 24 through which the catheter 14 extends, a compression coil spring 25 concentrically received around the catheter 14 within the cup element and a cylindrical gauge block 26 fixed to the catheter in compression imparting relationship to the spring 25 for free rotation within the cup element 23. The passage is sufficiently large to permit the catheter to freely rotate therein. Scale gradation indicia 27 are provided on the external surface of the block 26 for alignment with the left edge of the cup element 23, as viewed in FIG. 5.

Pulling force is applied to the catheter 14 of the FIG. 5 embodiment by gripping the cup element 23, as shown by the phantom line finger and thumb, designated 28 and 29. During such pulling, the cup element is free to turn about the longitudinal axis of the catheter and tension may be measured by observing the left edge of the cup element (as viewed in FIG. 5), relative to the indicia 27.

Figure 7:
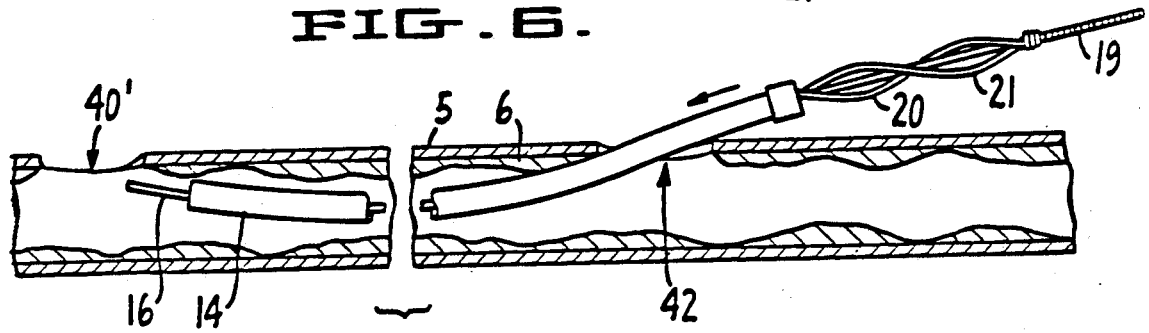
FIG. 7 is a similar view illustrating another method of preliminary emplacement.
Figure 8:
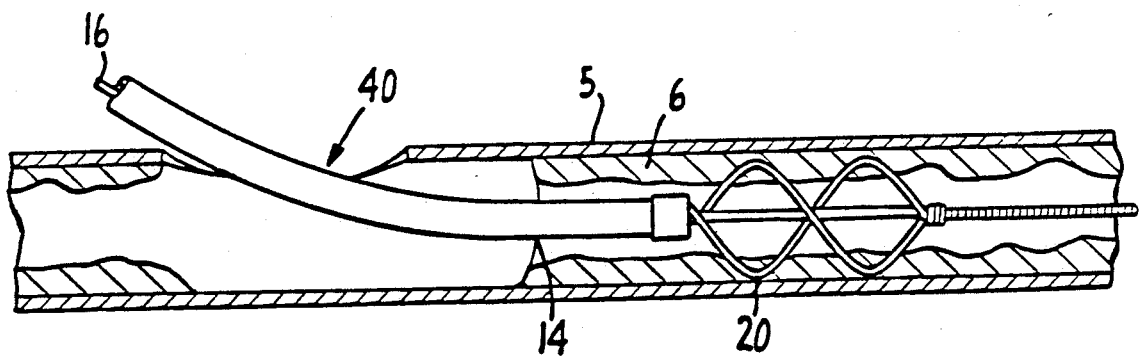
FIG. 8 is a view similar to FIG. 7 showing engagement of the shearing member with a deposit in preparation for removal of the deposit.
Figure 9:
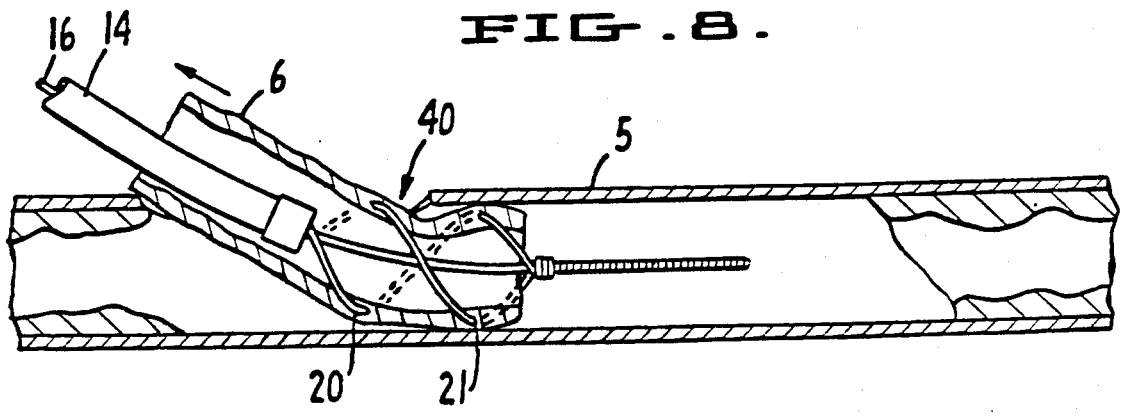
FIG. 9 is a view similar to FIG. 8 illustrating shearing and removal of the deposit from the artery.

FIGS. 6–9 illustrate the use of the apparatus of this invention in removing arteriosclerotic deposits from an artery 5. In one embodiment of the method, as shown in FIG. 6, the artery is prepared for treatment by making an incision 40 adjacent to the arteriosclerotic deposit 6. After incision, the apparatus is emplaced by introducing its distal end into the incision with the shearing member 18 in a radially contracted configuration. During insertion, the handle 10 may be rotated axially to reduce the torquing force of the apparatus on the artery 5 as the apparatus is introduced. Once a desired length of deposit 6 has been traversed, the shearing member 18 is radially expanded, as shown in FIG. 8, to press firmly against and engage the deposit 6 to be removed. Following this engagement, the apparatus is withdrawn, thereby shearing away that portion of the deposit 6 previously traversed, as shown in FIG. 9. Withdrawal is affected by pulling the cup 15 to engage the grip 12, thus permitting the grip to rotate within the cup as the apparatus is withdrawn and avoiding the application of torsional forces to the apparatus.

In an alternative embodiment of the method, shown in FIG. 7, two preparatory incisions, proximal 40' and distal 42, are made so as to bracket that portion of the deposit 6 to be removed. The handle 10, grip 12, and cup 15 are then removed and the apparatus is emplaced in the artery 5 by introducing its proximal end through the distal incision 42. Once inserted, the apparatus is threaded through the artery 6 until the proximal incision 40' is reached, at which point the proximal end of the apparatus is passed out of the artery 5 through incision 40. The apparatus may then be positioned as in the embodiment above until an appropriate length of deposit 6 lies between the shearing member 18 and the proximal incision 40'. Upon replacement, the handle 10, grip 12, and cup are reattached to the apparatus. The deposit 6 is then sheared from the artery 5 as described in the previous embodiment. The FIGS. 6 and 7 methods are similar in use in that the shearing member 18 is introduced into the artery in a radially contracted condition and expanded once in place within the deposit.

It should be appreciated that the apparatus shears the section of the deposit engaged thereby from the vessel wall, as contrasted to slicing it away. Radial expansion of the helical loops is effected in such a way that the loops embed in the deposit and do not cut therethrough so as to abrade the vessel wall. The loops do not slice along the interface of the deposit and the vessel wall, as is common in many endarterectomy apparatuses.

For an elongate deposit, the process of gripping and shearing sections of the deposit and removing them from the vessel is successively repeated until the entire length of the deposit is removed. The length of each section removed is chosen to minimize the number of times the process must be repeated, while at the same time assuring that the section may be sheared away with relative ease, without damaging the vessel or surrounding tissue.

The process using an apparatus with a shear force gauge as shown in FIG. 5 is the same as that described above, with the addition that the gauge is monitored to detect and limit the shear force applied through the apparatus. Such monitoring may be done visually by observing the position of the indicia 27 relative to the cup 12A. The shear force limit is chosen so as to assure that the apparatus will not injure the vessel being treated or the surrounding tissue.

Conclusion

Although preferred embodiments of the invention have been illustrated and described, it should be understood that the invention is not intended to be limited to the specifics of such embodiments, but rather defined by the accompanying claims.

We claim:

1. An endarterectomy instrument for removing an arteriosclerotic deposit adhered around the interior of an artery, said instrument comprising:

a flexible catheter having a proximal and a distal end;

a flexible guidewire having a proximal and a distal end, said guidewire slidably extending through and protruding from said catheter and having affixed to its proximal end a handle;

collapsible plaque gripping and shearing means comprising at least one flexible wire having a first end affixed to the distal end of said guidewire and a second end affixed to the distal end of said catheter, said means being variably expansible and contractible by longitudinal movement of said guidewire relative to said catheter between a first reduced diameter condition of a cross-section enabling the means to be passed through the artery and into the deposit without abrading the artery and a second expanded diameter condition embedded in gripping engagement with the deposit without substantial contact of the means with the artery; and, a shear force gauge to apply pulling force to the catheter and measure the pulling force applied to the plaque gripping and shearing means through the catheter, said gauge comprising:

a gauge block affixed to the proximal end of the catheter, said block having gradation indicia on the external surface thereof;

a pulling member slidably and rotatably received on the catheter adjacent the distal end thereof, said member having a portion thereof alignable with the indicia on the block; and a compression coil spring received on the catheter intermediate the gauge block and pulling member.

2. A method for removing an arteriosclerotic deposit adhered around the interior of an artery, said method comprising:

providing an endarterectomy device comprising first and second telescopically interrelated members having secured therebetween a resilient wire capable of assuming a radially expanded configuration upon relative movement of said members in a first direction and assuming a radially contracted condition upon relative movement of said members in a second direction;

making an incision in an artery adjacent to the deposit;

introducing the endarterectomy device into the artery through said incision with the wire radially contracted by movement of said telescopically interrelated members in the second direction to pass the wire through the artery without abrading the interior thereof;

feeding the endarterectomy device longitudinally of said artery to emplace the wire within the deposit;

radially expanding the wire by movement of said telescopically interrelated members in the first direction to embed the wire in gripping engagement with the deposit without substantial contact of the wire with the artery; and pulling the device through said incision to withdraw the device from the artery with the wire in the radially expanded condition, thereby traversing and shearing away at least a portion of the deposit and removing said portion from the artery.

3. A method for removing an arteriosclerotic deposit adhered around the interior of an artery, said method comprising:

providing an endarterectomy device having a proximal end and a distal end and comprising first and second telescopically interrelated members having secured therebetween a resilient wire capable of assuming a radially expanded configuration upon relative movement of said members in first direction and assuming a radially contracted condition upon relative movement of said members in a second direction;

making a proximal and a distal incision in an artery adjacent to the deposit;

introducing the proximal end of said endarterectomy device into the artery through the distal incision;

feeding the proximal end longitudinally through said artery toward and out of the proximal incision;

introducing the distal end of said device through the distal incision, with the wire radially contracted by movement of said telescopically interrelated members in the second direction to pass the wire through the artery without abrading the interior thereof, by pulling said device longitudinally through said artery from the proximal incision, thereby emplacing the endarterectomy device within said artery and the wire within deposit therein;

radially expanding the wire by movement of said telescopically interrelated members in the first direction to embed the wire in gripping engagement with the deposit without substantial contact of the wire with the artery; and pulling the device through the proximal incision to withdraw the device from the artery with the wire in the radially expanded condition, thereby traversing and shearing away at least a portion of the deposit.

* * * * *